United States Patent [19]

Miller et al.

[11] 4,413,003

[45] Nov. 1, 1983

[54] β-HYDROXYARYLETHYLIMIDAZOLES

[75] Inventors: George A. Miller, Maple Glen; Hak-Foon Chan, Doylestown, both of Pa.

[73] Assignee: Rohm and Haas Company, Philadelphia, Pa.

[21] Appl. No.: 820,274

[22] Filed: Jul. 29, 1977

[51] Int. Cl.$^3$ .................. A01N 43/50; C07D 233/64
[52] U.S. Cl. .................................. 424/273 R; 548/341
[58] Field of Search ........................ 548/341; 424/273

[56] References Cited

U.S. PATENT DOCUMENTS

| | | | |
|---|---|---|---|
| 3,531,494 | 9/1970 | Adolphi et al. | 260/309 |
| 3,679,697 | 7/1972 | Kreider et al. | 548/341 |
| 3,682,951 | 8/1972 | Kreider | 548/341 |
| 4,150,153 | 4/1979 | Walker | 548/341 X |

FOREIGN PATENT DOCUMENTS 1940388  9/1977  Fed. Rep. of Germany.

OTHER PUBLICATIONS

Godefroi et al., J. Med. Chem., vol. 12 (1969) pp. 784–791.
Cooper et al., Tetrahedron Let., vol. 45 (1971) pp. 4321–4324.
Thizy et al., Chemical Abstracts, vol. 84 (1976) 13,501y.

*Primary Examiner*—Richard Raymond
*Attorney, Agent, or Firm*—Polly E. Ramstad

[57] ABSTRACT

This invention relates to β-hydroxyarylethylimidazoles, their enantiomorphs, acid addition salts and metal salt complexes. This invention also relates to the method of preparation and use of these compounds. These compounds and salts thereof are highly active broad-spectrum systemic fungicides effective in controlling phytopathgogenic fungi such as barley net blotch (*Helminthosporium teres*), grey mold (*Botrytis cinerea*), bean powdery mildew (*Erysiphe polygoni*), grape downy mildew (*Plasmopora viticola*), rice blast (*Piricularia oryzae*), tomato late blight (*Phytophthora infestans*), and wheat stem rust (*Puccinia graminis* f. sp. *tritici* race 15B-2).

13 Claims, No Drawings

β-HYDROXYARYLETHYLIMIDAZOLES

SUMMARY OF THE INVENTION

This invention relates to compounds of the formula

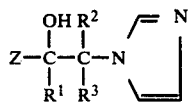
(I)

wherein Z is an aryl or substituted aryl group; $R^1$, $R^2$ and $R^3$ are independently a hydrogen atom, a cyano group, an alkyl group, a cycloalkyl group, an alkenyl group, a cycloalkenyl group, an alkynyl group, an aryl or substituted aryl group, an aralkyl or substituted aralkyl group; or $R^1$ and Z when taken together form the group

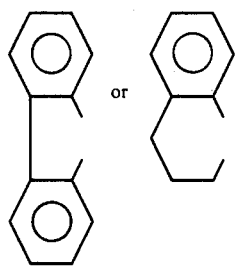

with the provision that when both $R^2$ and $R^3$ are hydrogen atoms, then $R^1$ is a cyano group, an alkyl group, a cycloalkyl group, an alkenyl group, a cycloalkenyl group, an alkynyl group, an aryl group or a substituted aryl group, an aralkyl or substituted aralkyl group; and the agronomically acceptable enantiomorphs, acid addition salts and metal salt complexes thereof. This invention also relates to the method of preparation of the compounds and salts of this invention as well as their use as broad-spectrum fungicides.

DETAILED DESCRIPTION OF THIS INVENTION

This invention relates to hydroxyarylethylimidazoles, enantiomorphs, acid addition salts and metal salt complexes thereof as well as their methods of preparation and use as highly active broad-spectrum systemic fungicides. In particular, this invention relates to compounds of the formula

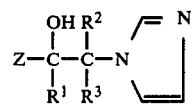
(II)

wherein Z is an optionally substituted ($C_6$ to $C_{10}$) aryl group; $R^1$, $R^2$ and $R^3$ are independently a hydrogen atom, a cyano group, a ($C_1$ to $C_{12}$) alkyl group, a ($C_3$ to $C_8$)cycloalkyl group, a ($C_2$ to $C_8$) alkenyl group, a ($C_5$ to $C_8$) cycloalkenyl group, a ($C_2$ to $C_8$) alkynyl group, an optionally substituted ($C_6$ to $C_{10}$) aryl group, or an optionally substituted ($C_7$ to $C_{14}$) aralkyl group or $R^1$ and Z when taken together form the group

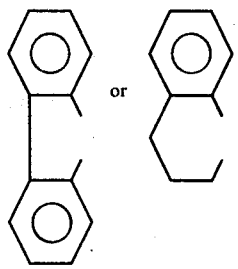

provided that when both $R^2$ and $R^3$ are a hydrogen atom, then $R^1$ is a cyano group, a ($C_1$ to $C_{12}$) alkyl group, a ($C_3$ to $C_8$) cycloalkyl group, a ($C_2$ to $C_8$) alkenyl group, a ($C_5$ to $C_8$) cycloalkenyl group, a ($C_2$ to $C_8$) alkynyl group, an optionally substituted ($C_6$ to $C_{10}$) aryl group, or an optionally substituted ($C_7$ to $C_{14}$) aralkyl group, and the agronomically acceptable enantiomorphs, acid addition salts and metal salt complexes thereof.

In the definition of the substituents Z, $R^1$, $R^2$ and $R^3$ in the present specification and claims, the term "aryl" is meant to define an aromatic ring structure of from 6 to 10 carbon atoms, preferably a phenyl or naphthyl group which is optionally substituted with up to three substituents, preferably with up to two substituents, selected from the group consisting of halogen, nitro, trihalomethyl, cyano, ($C_1$ to $C_4$) alkyl, ($C_1$ to $C_4$) alkoxy, ($C_1$ to $C_4$) alkylthio, ($C_1$ to $C_4$) alkylsulfinyl, ($C_1$ to $C_4$) alkylsulfonyl, phenoxy, phenylthio, phenylsulfinyl, phenylsulfonyl, and phenoxy, phenylthio, phenylsulfinyl or phenylsulfonyl substituted with up to two substituents selected from the group consisting of halogen, nitro, trifluoromethyl, cyano, methyl, methoxy, methylthio, methylsulfinyl and methylsulfonyl. Typical "aryl" and "substituted aryl" groups encompassed by this invention include phenyl, naphthyl, chlorophenyl, bromophenyl, fluorophenyl, iodophenyl, nitrophenyl, trifluoromethylphenyl, trichloromethylphenyl, cyanophenyl, tolyl, anisyl, methylthiophenyl, ethylthiophenyl, methylsulfinylphenyl, methylsulfonylphenyl, phenoxyphenyl, phenylthiophenyl, phenylsulfinylphenyl, phenylsulfonylphenyl, chlorophenoxyphenyl, bromophenoxyphenyl, fluorophenoxyphenyl, iodophenoxyphenyl, nitrophenoxyphenyl, trifluoromethylphenoxyphenyl, 2-cyanophenoxyphenyl, tolyloxyphenyl, anisyloxyphenyl, methylthiophenoxyphenyl, methylsulfinylphenoxyphenyl, methylsulfonylphenoxyphenyl, chlorophenylthiophenyl, bromophenylthiophenyl, fluorophenylthiophenyl, 2-methyl-4-chlorophenyl, 2-bromo-4-trifluoromethylphenyl, 2-methoxy-4-methylsulfonylphenylsulfonylphenyl, 2,4,6-trichlorophenyl, 2-nitro-3,5-dichlorophenyl, 3,4,5-trichlorophenyl, 2,3,4-trichlorophenyl, 2-methyl-4,5-dimethoxyphenyl, 2,4-dimethylsulfonylmethyl, 3,5-diphenoxyphenyl, 2,3-dimethylphenyl, 3,4-difluorophenyl, 2,5-diiodophenyl and the like.

In the definition of the substituents $R^1$, $R^2$ and $R^3$ in the present specification and claims the term "aralkyl" is meant to define an aralkyl group of from 7 to 14 carbon atoms the alkyl portion of which is from 1 to 4 carbon atoms which can be branched or straight chained while the aryl portion is meant to be defined as in the above definition of "aryl". Typical "aralkyl" and "substituted aralkyl" groups encompassed by this invention include benzyl, naphthylmethyl, phenethyl, phenylpropyl, naphthylpropyl, phenylisopropyl, phenylbutyl, naphthylbutyl, phenyl-sec-butyl, phenyl-tert-butyl, phenylpentyl, phenylisopentyl, phenylneopentyl, naphthylmethyl, chlorobenzyl, bromobenzyl, fluorobenzyl, iodobenzyl, nitrobenzyl, trifluoromethylbenzyl, trichloromethylbenzyl, cyanobenzyl, methylbenzyl, methoxybenzyl, methylthiobenzyl, ethylthiobenzyl, methylsulfinylbenzyl, methylsulfonylbenzyl, phenoxybenzyl, phenylthiobenzyl, phenylsulfinylbenzyl, phenylsulfonylbenzyl, chlorophenoxybenzyl, bromophenoxybenzyl, fluorophenoxybenzyl, iodophenoxybenzyl, nitrophenoxybenzyl, trifluoromethylphenoxybenzyl, cyanophenoxybenzyl, tolyloxybenzyl, anisyloxybenzyl, methylthiophenoxybenzyl, methylsulfinylphenoxybenzyl, methylsulfonylphenoxybenzyl, chlorophenylthiobenzyl, bromophenylthiobenzyl, fluorophenylthiobenzyl, 2-methyl-4-chlorobenzyl, 2-bromo-4-trifluoromethylbenzyl, 2-methoxy-4-methylsulfonylphenylsulfonylbenzyl, 2,4,6-trichlorobenzyl, 2-nitro-3,5-dichlorobenzyl, 3,4,5-trichlorobenzyl, 2,3,4-trichlorobenzyl, 2-methyl-4,5-dimethoxybenzyl, 2,4-dimethylsulfonylbenzyl, 3,5-diphenoxybenzyl, 2,3-dimethylbenzyl, 3,4-difluorobenzyl, 2,5-diiodobenzyl and the like.

The term "alkyl" as utilized in the definition of the $R^1$, $R^2$ and $R^3$ substituents in the present specification and claims is meant to define an alkyl group of from 1 to 12 carbon atoms which can be branched or straight chained. Typical alkyl groups encompassed by this invention include methyl, ethyl, propyl, isopropyl, n-butyl, sec-butyl, tert-butyl, n-pentyl, isopentyl, sec-pentyl, neopentyl, n-hexyl, sec-hexyl, heptyl, octyl, nonyl, decyl, undecyl, dodecyl and the like.

The acids which can be utilized in making the acid addition salts of the present invention include hydrochloric, hydrobromic, nitric, sulfuric, phosphoric, hydroiodic, hydrofluoric, perchloric, p-toluenesulfonic, methanesulfonic, acetic, citric, tartaric, malic, maleic, oxalic, fumaric, phthalic and the like.

Another embodiment of this invention is the metal salt complexes of the formula

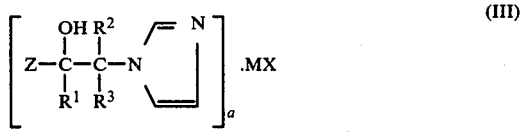

(III)

wherein Z, $R^1$, $R^2$ and $R^3$ are as defined in Formula (II) above a is an integer from 1 to 4 and M is a cation selected from Group IIA, IB, IIB, VIB, VIIB and VIII of the Periodic Table and X is an anion counterion selected in such a manner that the sum of the valence charges of the cation M and the anion X equals zero.

Typical cations encompassed by this invention are magnesium, manganese, copper, nickel, zinc, iron, cobalt, calcium, tin, cadmium, mercury, chromium, lead, barium and the like.

Typical anions encompassed by this invention are chloride, bromide, iodide, fluoride, sulfate, bisulfate, perchlorate, nitrate, nitrite, phosphate, carbonate, bicarbonate, acetate, citrate, oxalate, tartarate, malate, maleate, fumarate, p-toluenesulfonate, methanesulfonate, (mono) or (di) ($C_1$ to $C_4$) alkyldithiocarbamate, ($C_1$ to $C_4$) alkylene-bis-dithiocarbamate and the like.

A preferred embodiment of this invention is the compounds, agronomically acceptable enantiomorphs, salts and complexes of Formulas (II) and (III) wherein Z is a phenyl or naphthyl group, preferably a phenyl group, optionally substituted with up to three substituents, preferably with up to two substituents, selected from the group consisting of halogen, nitro, trihalomethyl, cyano, ($C_1$ to $C_4$) alkyl, ($C_1$ to $C_4$) alkoxy, ($C_1$ to $C_4$) alkylthio, ($C_1$ to $C_4$) alkylsulfinyl, ($C_1$ to $C_4$) alkylsulfonyl, phenoxy, phenylthio, phenylsulfinyl, phenylsulfonyl, and phenoxy, phenylthio, phenylsulfinyl or phenylsulfonyl substituted with up to two substituents selected from the group consisting of halogen, nitro, trifluoromethyl, cyano, methyl, methoxy, methylthio, methylsulfinyl and methylsulfonyl; $R^1$, $R^2$ and $R^3$ are independently a hydrogen atom, a cyano group, a ($C_1$ to $C_8$) alkyl group, a ($C_3$ to $C_6$) cycloalkyl group, a ($C_2$ to $C_4$) alkenyl group, a ($C_5$ or $C_6$) cycloalkenyl group, a ($C_2$ to $C_4$) alkynyl group, a phenyl group optionally substituted with up to two substituents selected from the group consisting of halogen, nitro, trihalomethyl, cyano, methyl, methoxy, methylsulfinyl and methylsulfonyl, or a benzyl or phenethyl group optionally substituted with up to two substituents selected from the group consisting of halogen, nitro, trihalomethyl, cyano, methyl, methoxy, methylsulfinyl and methylsulfonyl; or $R^1$ and Z when taken together form the group

provided that when both $R^2$ and $R^3$ are a hydrogen atom, then $R^1$ is a cyano group, a ($C_1$ to $C_8$) alkyl group, a ($C_3$ to $C_6$) cycloalkyl group, a ($C_2$ to $C_4$) alkenyl group, a ($C_5$ or $C_6$) cycloalkenyl group, a ($C_2$ to $C_4$) alkynyl group, a phenyl group optionally substituted with up to two substituents selected from the group consisting of halogen, nitro, trihalomethyl, cyano, methyl, methoxy, methylsulfinyl and methylsulfonyl or a benzyl or phenethyl group optionally substituted with up to two substituents selected from the group consisting of halogen, nitro, trihalomethyl, cyano, methyl, methoxy, methylsulfinyl and methylsulfonyl.

A more preferred embodiment of this invention is the compounds wherein Z is a phenyl group optionally substituted with up to three substituents selected from the group consisting of halogen, preferably chlorine, ($C_1$ to $C_4$) alkyl, preferably methyl and ($C_1$ to $C_4$) alkoxy preferably methoxy; $R^1$ is ($C_1$ to $C_8$) alkyl, phenyl or benzyl; $R^2$ is hydrogen, phenyl or chlorophenyl, preferably hydrogen or 2-chlorophenyl; and $R^3$ is hydrogen.

Typical compounds encompassed by the present invention include:

1-[2-hydroxy-2-methyl-2-(2,4,6-trichlorophenyl)ethyl]imidazole

1-[2-hydroxy-2-n-butyl-2-(2-methyl-4-trifluoromethylphenyl)ethyl]imidazole

1-[2-hydroxy-2-phenyl-2-(3,4-dimethoxyphenyl)ethyl]imidazole

1-[2-hydroxy-2-benzyl-2-(2,3-dichlorophenyl)ethyl]imidazole

1-[2-hydroxy-2-(2-chlorophenyl)-2-(2,5-dinitrophenyl-
)ethyl]imidazole
1-[2-hydroxy-2-(4-bromophenyl)-2-(3,5-dimethylsul-
fonylphenyl)ethyl]imidazole
1-[2-hydroxy-1,1-dimethyl-2-(2,4-ditrifluoromethyl-
phenyl)ethyl]imidazole
1-[2-hydroxy-2-phenyl-1-methyl-2-(3,4,5-trimethyl-
phenyl)ethyl]imidazole
1-[2-hydroxy-1,2-bis-n-butyl-2-(2,4-di-tert-butylphenyl-
)ethyl]imidazole
1-[2-hydroxy-1,1,2-tris-phenyl-2-(2,4-dichlorophenyl)e-
thyl]imidazole
1-[2-hydroxy-1,1,2-tris-benzyl-2-(3,4-dinitrophenyl)e-
thyl]imidazole
1-{2-hydroxy-2-methyl-2-[4-(4-methylsulfonylphenyl)
sulfonylphenyl]ethyl}imidazole
1-[2-hydroxy-2-isopropyl-2-(3-phenoxyphenyl) ethyl-
]imidazole
1-[2-hydroxy-2-neopentyl-2-(4-phenylthiophenyl)ethyl-
]imidazole
1-[2-hydroxy-2-sec-hexyl-2-(4-phenylsulfinylphenyl)e-
thyl]imidazole
1-[2-hydroxy-2-n-heptyl-2-(4-phenylsulfonylphenyl)e-
thyl]imidazole
1-{2-hydroxy-2-n-octyl-2-[4-(4-chlorophenoxy)phenyl-
]ethyl}imidazole
1-[2-hydroxy-2-(2-chloronapthyl)ethyl]imidazole
1-[2-hydroxy-2-(1-bromonapthyl)ethyl]imidazole
1-[2-hydroxy-1,2-dimethyl-2-(2-naphthyl)ethyl-
]imidazole
1-[2-hydroxy-2-cyclohexyl-2-(2,4,5-trimethoxyphenyl-
)ethyl]imidazole
1-[2-hydroxy-2-cyclohexenyl-2-(2,4-trichloromethyl-
phenyl)ethyl]imidazole
1-[2-hydroxy-2-cyano-2-(2,4-dinitrophenyl)ethyl-
]imidazole
1-[2-hydroxy-2-propargyl-2-(2,4-difluorophenyl)ethyl-
]imidazole
1-[2-hydroxy-2-allyl-2-(2,6-dichlorophenyl)ethyl-
]imidazole.
and the agronomically acceptable enantiomorphs, acid
addition salts and metal salt complexes thereof.

The compounds of the present invention can be prepared by general synthetic routes. In particular, the compounds of the present invention can be prepared by the following reaction sequence.

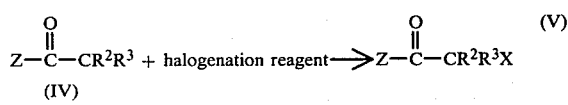

The appropriately substituted acetophenone and methyl-α or β-naphthyl ketone (IV) are readily available starting materials and can be prepared by standard Friedel-Crafts reactions. These ketones can be halogenated with molar or excess amounts of standard halogenation reagents such as chlorine, bromine, N-chlorosuccinimide, N-bromosuccinimide and the like, at temperatures from about 0° C. to about 175° C. either neat or in an appropriate inert solvent such as chloroform, carbon tetrachloride, 1,1,2,2-tetrachloroethane, dichlorobenzene and the like. The resultant α-haloketones (V) are then coverted to halohydrins by one of the following reaction sequences.

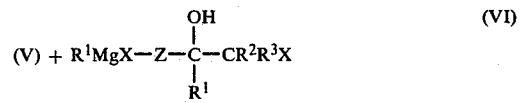

The α-haloketone (V) can be converted into a halohydrin by standard Grignard reactions, i.e. by reaction with a molar or excess amount of an aryl or alkyl magnesium halide in an anhydrous inert solvent such as diethyl ether, tetrahydrofurane, dioxane and the like, at temperatures from about −20° C. to about 120° C. followed by acid hydrolysis to give the halohydrin (VI). In the case of highly hindered α-haloketones, reduction takes place instead of alkylation and in such cases the following reaction sequence can be utilized.

The α-haloketones (V) can be converted to the halohydrin as follows:

In this reaction the α-haloketone is reacted with a molar or excess amount of an alkyl or aryl lithium organometallic compounds in an anhydrous inert solvent such as hexane, benzene, and the like, at temperatures from about −80° C. to about 30° C. followed by acid hydrolysis to give the halohydrin (VI).

Alternatively, the halohydrins can be prepared by the following reaction sequence.

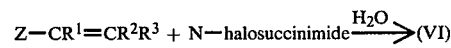

The appropriately substituted ethylene compound is reacted with a molar or excess amount of an N-halosuccinimide, in an appropriate solvent system such as aqueous, ketone or tertiary alcohol systems and the like, at temperatures from about 0 C. to about 150 C. to give the halohydrin (VI) which can then be used in the following reaction sequence.

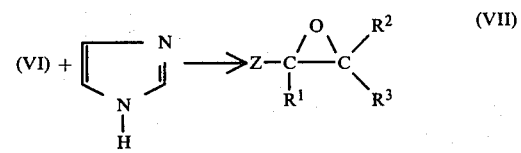

The halohydrin (VI) is reacted with a molar amount of imidazole, either neat or in an appropriate solvent such as dimethylsulfoxide, dimethylformamide and the like, at temperatures from about 0° C. to about 150° C. to give the epoxide (VII) which is then used in the following reaction sequence:

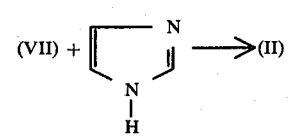

The epoxide is then reacted with an additional molar or excess amount of imidazole either neat or in an appropriate solvent such as dimethylsulfoxide, dimethylformamide and the like, at temperatures from about 0° C. to about 150° C. to give the compound (II) of the present invention. Alternatively, the halohydrin can be reacted with at least 2 moles of imidazole to form the compound (II) of the present invention without isolating the epoxide (VII) intermediate.

Alternatively, the desired product (II) can be prepared from the reaction of a suitably substituted ketone and dimethyl sulfoxonium ylide in an appropriate solvent such as dimethyl sulfoxide at temperatures from about 15° to about 100° to give an epoxide of Formula (VII); which can then be reacted with imidazole as above, to give the desired product.

The acid addition salts of the β-hydroxyarylethylimidazoles of the present invention can be prepared by standard techniques well-known in the art. For example, the β-hydroxyarylethylimidazole of Formula (II) can be dissolved in an appropriate solvent such as diethyl ether, tetrahydrofuran, ethanol, methanol and the like or combinations thereof, and treated with an equivalent or excess amount of a mineral or organic acid which may or may not be dissolved in an appropriate solvent. The mixture is then either cooled or evaporated to give the salt which can either be used as such or recrystallized from an appropriate solvent or combination of appropriate solvents.

The metal salt complexes of the above α-hydroxyarylethylimidazoles can be prepared by adding dropwise, with stirring, a stoichiometric amount of a metal salt dissolved in an appropriate solvent or combination of solvents to a solution of the β-hydroxyarylethylimidazole of Formula (II) dissolved in a similarly appropriate solvent or combination of solvents. The reaction mixture is briefly stirred and the solvent is removed under reduced pressure to give the metal salt complex of the respective β-hydroxyarylethylimidazoles of Formula (III).

The metal salt complexes can also be prepared by mixing stoichiometric or excess amounts of the metal salt and a β-hydroxyarylethylimidazole of Formula (II) in the desired amount of solvent containing appropriate adjuvants just prior to spraying the plants. Adjuvants that may be included in the "in-situ" preparation may be detergents, emulsifiers, wetting agents, spreading agents, dispersing agents, stickers, adhesives, and the like which are used in agricultural applications.

Solvents that can be utilized in these procedures include any polar solvent e.g., water, methanol, ethanol, isopropanol, or ethylene glycol and any aprotic dipolar solvent e.g., dimethylsulfoxide, acetonitrile, dimethylformamide, nitromethane or acetone.

The metal salt cations that can be used in these procedures can be selected from the group consisting of calcium, magnesium, manganese, copper, nickel, zinc, iron, cobalt, tin, cadmium, mercury, chromium, lead, barium, and the like.

Any appropriate anion e.g., chloride, bromide, iodide, sulfate, bisulfate, phosphate, nitrate, perchlorate, carbonate, bicarbonate, hydrosulfide, hydroxide, acetate, oxalate, malate, citrate, tartarates, maleate and the like may be utilized as the counterion in the metal salt.

Any metal containing fungicides can also be used as complexing agents used in place of metal salts. Typical metal containing fungicides that can be utilized in these procedures are: (a) dithiocarbamates and derivatives such as: ferric dimethyldithiocarbamate (ferbam), zinc dimethyldithiocarbamate (ziram), manganese ethylenebisdithiocarbamate (maneb) and its coordination product with zinc ion (mancozeb), zinc ethylenebisdithiocarbamate (zineb); (b) copper-based fungicides such as cuprous oxide, copper oxychloride, copper naphthenate, and Bordeaux mixture; and (c) miscellaneous fungicides such as: phenylmercuri acetate, N-ethyl-mercuri-3,4,5,6,7,7-hexachlorophthalimide, phenylmercuri monoethanol-ammonium lactate, nickel-containing compounds and calcium cyanamide.

The compounds of this invention possess an assymetric carbon atom and thus are made as racemic mixtures. The d and l enantiomorphs in these racemic mixtures can be separated via standard techniques such as fractional crystallization with d-tartaric acid, l-tartaric acid, l-quinic acid and the like followed by basification and extraction of the active d or l enantiomorph free base.

The following examples are provided merely to illustrate the methods of preparation of the compounds of the present invention. These examples are not meant to be considered, in any way, as limitations of the breadth and scope of the present invention. The temperatures expressed in these examples are in degrees centigrade.

EXAMPLE 7

Preparation of
1-[2-Hydroxy-1,2-bis-(2-chlorophenyl)ethyl]imidazole

A. 2,2'-Dichloro-α,α'-epoxydibenzyl

This material is prepared according to the procedure published in *Organic Synthesis*, Collective Volume I, page 358.

B. 1-[2-Hydroxy-1,2-bis-(2-chlorophenyl)ethyl]imidazole

A mixture of 11 g (0.04 m) of 2,2'-dichloro-α,α'-epoxybibenzyl and 15 g (0.22 m) of imidazole is heated at 160° for 1½ hours. The reaction is cooled, diluted with water, and extracted with ether. The combined ether extracts are washed with water, then saturated sodium chloride solution, and dried over $MgSO_4$. Solvent is evaporated to give 12 g of a gummy solid, mp 62°–68°.

nmr($CDCl_3$): δ5.9 (m, 2H), 6.8–8.0 (complex multiplets, 12H)

EXAMPLE 8

Preparation of
1-[2-Hydroxy-2-(2,4-dichlorophenyl)hexyl]imidazole

A. 1-Chloro-2-(2,4-dichlorphenyl)hexan-2-ol

Into a 500 ml four-necked flask equipped with a thermometer, a condenser, a mechanical stirrer, an addition funnel, and a nitrogen inlet tube are placed 102 ml (0.2 m, 1.97 M solution in hexane) of n-butyllithium. This solution is cooled to −60° with an acetone-dry ice bath. 2,4-Dichlorphenacyl chloride (44.7 g, 0.2 m) dissolved in 250 ml of ether is then added dropwise. The temperature is maintained below −55° throughout the reaction. After the addition, the reaction is allowed to warm gradually to −10° and then poured into a mixture containing 250 ml of saturated ammonium chloride and 250 ml of 10% hydrochloric acid solution. The layers are separated and the aqueous layer is extracted with 100 ml of ether. The combined ether extracts are washed with 10% hydrochloric acid, saturated sodium chloride solution, and dried over $MgSO_4$. Solvent is evaporated to give 52 g of a pale yellow oil. Vacuum distillation (100°–120°/0.2 mm) affords 44 g of pure product.

nmr ($CDCl_3$): δ0.6–2.5 (m, 9H), 2.8 (S, 1H), 4.2 (q, 2H), 7.2–7.9 (m, 3H)

B. 1-[2-Hydroxy-2-(2,4-dichlorophenyl)hexyl]imidazole

A mixture of 40 g (0.14 m) of 1-chloro-2-(2,4-dichlorophenyl)hexan-2-ol and 38.6 g (0.57 m) of imidazole in 10 ml of dimethyl formamide is heated at 160° for one hour. The reaction mixture is cooled, poured into 300 ml of water and extracted with ether. The combined ether extracts are washed with water, then saturated sodium chloride solution and dried over MgSO$_4$. Solvent is evaporated to give 42 g of a gummy brown solid, mp 78°–80°.

nmr (CDCl$_3$): δ0.5–3.0 (complex multiplets, 9H), 4.5 (q, 2H) 5.4 (S, 1H, exchangeable), 6.6–7.8 (m, 6H)

EXAMPLE 9

Preparation of 1-[2-Hydroxy-2-phenyl-2-(2,4-dichlorophenyl)ethyl]imidazole

A. 1-Phenyl-1-(2,4-dichlorophenyl)-2-chloroethanol

Into a 1 liter three-necked flask are placed 5.35 g (0.22 m) of magnesium turning and 50 ml of anhydrous ether. Bromobenzene (34.5 g, 0.22 m) in 100 ml of ether is then added dropwise under nitrogen. When the reaction started, the rate of addition is controlled so that ether remained refluxing gently. After the addition, the mixture is stirred for 10 minutes at room temperature and then cooled to 10° with an ice bath. To this phenyl magnesium bromide solution is added 44.7 g (0.2 m) of 2,4-dichlorophenacyl chloride dissolved in 100 ml of ether dropwise. The reaction mixture is stirred at room temperature for ½ hour followed by slow addition of dilute HCl solution (300 ml). The phases are then separated and the ether layer is washed with saturated sodium bicarbonate solution and dried over MgSO$_4$. Solvent is evaporated to give 56 g of a yellow oil. Vacuum distillation (156°/0.1 mm) affords 40 g of pure product.

nmr (CDCl$_3$): 3 4 (S, 1H, exchangeable), 4.36 (q, 2H), 7.2–7.9 (m, 8H)

B. 1-[2-Hydroxy-2-phenyl-2-(2,4-dichlorophenyl)thyl]imidazole (HFC 5:11)

A mixture of 10 g (0.033 m) of 1-phenyl-1-(2,4-dichlorophenyl)-2-chloroethanol and 10 g (0.147 m) of imidazole is heated at 110° C. for ½ hour. The reaction mixture is poured into water. The white solid precipitate is then collected by filtration and dried in a vacuum oven to give 5 g of pure product, mp 246°–8°.

nmr (CF$_3$COOH): δ5.4 g (q, 2H), 7.0–7.9 (complex multiplets, 11H), 8.4 (S, 1H)

EXAMPLE 11

Preparation of 1-hydroxy-1-(N-imidazolylmethyl)-1,2,3,4-tetrahydronaphthalene hydrochloride A. Spiro (1,2,3,4-tetrahydronaphthalene-1,2-oxiran)

In a 500 ml three-necked round-bottom flask equipped with a mechanical stirrer, a reflux condenser and a nitrogen inlet tube is placed 11.6 g (0.24 mol) of sodium hydride (50% dispersion in mineral oil). The mineral oil is removed by washing three times with n-hexane. The system is flushed with anhydrous nitrogen until the last trade of n-hexane is evaporated. Dimethyl sulfoxide (175 ml, freshly distilled from calcium hydride) is added, followed by the addition of trimethylsulfoxonium iodide (50 g, 0.23 mol) in small portions during 1½ hours period with occasional cooling with an ice bath. One hour after the addition is complete and hydrogen evolution ceased, a solution of 1-tetralone (26.8 g, 0.18 mol) in dimethyl sulfoxide is added over a 15 minute period at room temperature. The reaction mixture is heated at 55° for 2 hours, at room temperature overnight, and then poured into water and extracted with ether (2×150 ml). The combined ether extracts are washed with water and dried over MgSO$_4$. Solvent is evaporated to give 20.8 g of an oil. The nmr spectrum of this material is identical to that reported-P. A. Crooks and R. Szyndler, *Chemistry and Industry*, 1111 (1973).

B. 1-Hydroxy-1-(N-imidazolylmethyl)-1,2,3,4-tetrahydronaphthalene hydrochloride

In a 500 ml three-necked round-bottom flask equipped with a mechanical stirrer, an addition funnel, a Dean Stark trap, and a refluxing condenser, are placed 4.4 g (0.064 mol) of imidazole, 2.6 g (0.064 mol) of sodium hydroxide pellets, 75 ml dimethylsulfoxide, and 50 ml of toluene. The mixture is heated to 125° for 2 hours, and water formed in this reaction is azeotroped. The remaining toluene is then distilled. To this solution is added 10.4 g (0.065 mol) of crude spiro-(1,2,3,4-tetrahydronaphthalene-1,2-oxiran) dissolved in 25 ml of dimethyl sulfoxide dropwise at 115°. The reaction mixture is heated at 115° for 2 hours. It is then cooled to room temperature and poured into water and extracted with ether (2×150 ml). The combined ether extracts are washed with water and dried over MgSO$_4$. The drying agent is filtered and the etheral solution is acidified with dry hydrogen chloride to give 2.0 g of a solid, mp 167°–9°.

nmr (DMSO): 1.5–3.0 (complex multiplets, 7H), 4.6 (S, 2H), 7.0–8.0 (m, 7H), 9.2 (S, 1H)

Tables I and II give the structure, melting points in degrees centigrade and the elemental analysis of some of the more representative compounds encompassed by the present invention which were synthesized by the above procedures.

TABLE I $$\begin{array}{c} OH \quad R^2 \\ | \quad | \\ Z-C-C-N \\ | \quad | \\ R^1 \quad R^3 \end{array} \quad \begin{array}{c} \diagup = N \\ \diagdown \underline{\quad} \end{array} \cdot Y$$

| Example No. | Z | R$^1$ | R$^2$ | R$^3$ | Y |
|---|---|---|---|---|---|
| 1 | C$_6$H$_5$ | C$_4$H$_{9n}$ | H | H | — |
| 2 | C$_6$H$_5$ | C$_4$H$_{9n}$ | H | H | HNO$_3$ |
| 3 | C$_6$H$_5$ | C$_8$H$_{17n}$ | H | H | — |
| 4 | C$_6$H$_5$ | C$_8$H$_{17n}$ | H | H | HNO$_3$ |
| 5 | 4CH$_3$—C$_6$H$_4$ | CH$_3$ | H | H | — |
| 6 | 4CH$_3$O—C$_6$H$_4$ | CH$_2$C$_6$H$_5$ | H | H | — |
| 7 | 2Cl—C$_6$H$_4$ | H | 2Cl—C$_6$H$_4$ | H | — |
| 8 | 2,4Cl$_2$—C$_6$H$_3$ | C$_4$H$_{9n}$ | H | H | — |
| 9 | 2,4Cl$_2$—C$_6$H$_3$ | C$_6$H$_5$ | H | H | — |
| 10 | 2,3,4Cl$_3$—C$_6$H$_2$ | C$_4$H$_{9n}$ | H | H | HNO$_3$ |
| 11 | Z + R$^1$ = (naphthalene ring structure) | | H | H | HCl |

TABLE II

| Example No. | MP | Elemental Analysis - Cal'd (Found) | | | | |
|---|---|---|---|---|---|---|
| | | C | H | Cl | N | O |
| 1 | 131 (dec) | 73.73 (71.88) | 8.25 (8.20) | | 11.47 (10.23) | |
| 2 | 131 | 58.62 (59.44) | 6.89 (6.90) | | 13.67 (12.92) | |
| 3 | 122–3 | 75.96 (76.08) | 9.39 (9.44) | | 9.33 (9.48) | 5.33 (6.35) |
| 4 | 108–10 | 62.79 | 8.04 | | 11.56 | 17.61 |

TABLE II-continued

| Example No. | MP | \multicolumn{5}{c}{Elemental Analysis - Cal'd (Found)} |
|---|---|---|---|---|---|---|
| | | C | H | Cl | N | O |
| | | (62.19) | (8.13) | | (12.11) | (18.12) |
| 5 | Conc. | 72.19 | 7.45 | | 12.95 | |
| | | (71.41) | (7.67) | | (12.04) | |
| 6 | 188–90 | 74.00 | 6.54 | | 9.09 | 10.38 |
| | | (74.03) | (6.51) | | (9.46) | (10.72) |
| 7 | 62–8 | 61.28 | 4.24 | 21.28 | 8.41 | 4.80 |
| | | (61.80) | (4.35) | (20.46) | (9.49) | (4.83) |
| 8 | 78–80 | 57.52 | 5.79 | 22.64 | 8.94 | 5.11 |
| | | (56.52) | (5.65) | (23.74) | (8.58) | (6.05) |
| 9 | 246–8 | 61.28 | 4.24 | 21.28 | 8.41 | 4.80 |
| | | (60.95) | (4.28) | (21.62) | (8.70) | (4.76) |
| 10 | 165 (dec) | 43.87 | 4.42 | 25.90 | 10.23 | |
| | | (44.03) | (4.50) | (26.45) | (9.82) | |
| 11 | 164–8 | 63.99 | 5.76 | 13.50 | 10.66 | 6.09 |
| | | (60.07) | (6.10) | (13.00) | (9.90) | (7.74) |

The β-hydroxyarylethylimidazoles, enantiomorphs, acid addition salts and metal salt complexes of this invention are broad-spectrum fungicides which possess a high degree of activity against assorted phytopathogenic fungi. These compounds, enantiomorphs, salts and complexes are particularly effective at rates of application from about 50 to about 2000 ppm in controlling barley net blotch (*Helminthosporium teres*) on barley plants, grey mold (*Botrytis cinerea*) on faba beans, bean powdery mildew (*Erysiphe polygoni*) on bean plants, grape downy mildew (*Plasmopora viticola*) on grape seedlings, rice blast (*Piricularia oryzae*) on rice plants, tomato late blight (*Phytophthora infestans*) on tomato seedlings, and wheat stem rust (*Puccinia graminis* f. sp. *tritici* race 15B-2) on wheat seedlings.

In evaluating these compounds, a preliminary fungicidal evaluation is carried out using the compounds at 300 ppm and spraying the plants to run off in a carrier volume of about 150 gallons/acre.

The general procedure is to take potted plants in proper condition of growth for susceptibility to the fungal disease to be evaluated, to spray these on a moving belt and allow them to dry. The plants are then inoculated with the fungal spores and incubated until the disease has developed and the percent control is read or estimated.

The following test methods are employed in evaluating the fungicidal activity of the compounds, enantiomorphs, salts and complexes of this invention.

EXAMPLE A-Barley Net Blotch (*Helminthosporium teres*)

Barley plants (var. Wong) are trimmed to a height of approximately 2.5 inches, 24 hours prior to chemical application. This procedure provides plants of a uniform height and permits rapid inoculation of treated plants. The barley plants are inoculated by spraying the foliage of the plants with a hand sprayer until small droplets of the inoculum are observed on the leaves. Inoculated plants are incubated in a humid environment at 75°–80° F. for 24 hours prior to being placed in the greenhouse at 70°–75° F. Treatment comparisons are made 6 to 7 days after inoculation. Typical barley net blotch symptoms initially appear as irregular sunken water-soaked areas which become necrotic as the lesions enlarge. Certain of the β-hydroxyarylethylimidazoles of this invention demonstrate complete control over *Helminthosporium teres* at application rates of 300 ppm.

EXAMPLE B-Broad Bean Gray Mold Leaf Spot (*Botrytis cinerea*)

Broad bean plants (var. *Vicia faba*) are trimmed to a height of approximately 4.5 inches, 24 hours prior to chemical application. This procedure provides plants of a uniform height and permits rapid and uniform inoculation of the treated plants. Broad bean plants are inoculated by spraying the foliage with a herbicide belt sprayer. Inoculated plants are incubated in a humid environment at 75°–80° F. for 66 hours. Treatment comparisons are made 66 to 68 hours after inoculation. Typical broad bean gray mold leaf spot symptoms appear as regular circular to lanceolate lesions on plant leaves and stems. Certain of the β-hydroxyarylethylimidazoles of this invention demonstrate greater than 90% control over *Botrytis cinerea* at application rates of 300 ppm.

EXAMPLE C-Bean Powdery Mildew (*Erysiphe polygoni*)

Bean plants (var. Drawf Hort) are thinned to two plants per pot 24 hours prior to chemical application. Bean plants are inoculated by spraying the leaves and stems with inoculum until a uniform film of inoculum is observed on the plant. Inoculated plants are maintained under existing greenhouse conditions. Treatment comparisons are made 8 to 10 days after inoculation. Typical bean powdery mildrew symptoms are circular white mycelial mats (fructifications) on the leaf surface. Certain of the β-hydroxyarylethylimidazoles of this invention demonstrate complete control over *Erysiphe polygoni* at application rates greater than 300 ppm.

EXAMPLE D-Grape Downy Mildew (*Plasmopora viticola*)

Grape seedlings (var. Siebel 1000) 4 to 5 inches tall are used. *Plasmopora viticola* is cultured on grape leaves for 7 days at 65°–75° F. The grape plants are inoculated by spraying the leaves with a hand held air brush until small uniform droplets of inoculum are observed on the leaves. The inoculated plants are incubated in a humid environment at 65°–70° F. for 48 hours prior to being placed in a growth room. Typical grape downy mildew symptoms appear on the upper surface as pale-yellow spots variable in size and form, frequently circular without a distinct line of demarcation. Under humid conditions the lower leaf surface is covered by conspicuous fungal growth. Certain of the β-hydroxyarylethylimidazoles of this invention possess greater than 90% control over *Plasmopora viticola* at application rates of 300 ppm.

EXAMPLE E-Rice Blast (*Piricularia oryzae*)

Rice plants (var. Nova 66) are trimmed to a height of approximately 5 inches, 24 hours prior to chemical application. This procedure provides plants of uniform height and permits rapid inoculation of treated plants. Rice plants are inoculated by spraying the leaves and stems with an air brush until a uniform film of inoculum is observed on the leaves. The inoculated plants are incubated in a humid environment (75°–85° F.) for 24 hours prior to being placed in a greenhouse environment. Treatment comparisons are made 7 to 8 days after inoculation. Initial rice blast lesions appear as small brown necrotic spots on the foliage. The typical lesion is ecliptical, 1 to 2 cm. long with a large necrotic gray center and brown margins. Certain of the β-hydroxyarylethylimidazoles of this invention possess complete control over *Piricularia oryzae* at application rates of 300 ppm.

EXAMPLE F-Tomato Late Blight (*Phytophthora infestans*)

Tomato (var. Rutgers) seedlings, 2.5 to 3 inches tall, are fertilized with a water soluble fertilizer 4 to 5 days prior to chemical application to promote rapid succulent growth and better symptom expression. The spore suspension is applied with a DeVilbiss atomizer at 8 to 10 psi. air pressure onto the leaf undersurface until fine droplets are formed. Inoculated seedlings are placed in a humid environment at 60°-62° F. for 40 to 45 hours, prior to being placed in the greenhouse at 70°-75° F. Treatment comparisons are made 5 to 6 days after inoculation. Initially, typical tomato late blight symptoms appear as irregular, greenish-black, water-soaked patches which enlarge and become brown, with a firm corrugated surface. Severe infection will resemble frost damage. Certain of the β-hydroxyarylethylimidazoles of the present invention possess complete control over *Phytophthora infestans* at application rates of 300 ppm.

EXAMPLE G-Wheat Stem Rust (*Puccinia graminis* f. sp. *tritici* race 15B-2)

Seven-day-old wheat plants (var. Monon) are trimmed to approximately 2.5 inches, 24 hours prior to chemical application to provide a uniform plant height and to facilitate uniform inoculation. Wheat stem rust is cultured on wheat seedlings (var. Monon) for a period of 14 days under existing greenhouse conditions. Wheat plants are inoculated by applying the stem rust spore suspension, until run-off, with a DeVilbiss atomizer at 5 psi. air pressure. After inoculation, the plants are placed into a humid environment at approximately 68° F. A timer is used to permit 12 hours of continuous darkness followed by a minimum of 3 to 4 hours of light with an intensity of 500 foot candles. The temperature in the chamber should not exceed 85° F. At the end of the light period, the fogger is turned off and vented to allow the plants to dry slowly prior to being placed into a greenhouse environment. The plants are permitted to grow under greenhouse conditions for a period of 2 weeks prior to making treatment comparisons. Wheat stem rust is characterized by brick red spores in irregularly shaped sori on the leaves and stems of the wheat seedlings. Certain of the β-hydroxyarylethylimidazoles of the present invention possess complete control over *Puccinia graminis* f. sp. *tritici* race 15B-2 at application rates of 300 ppm.

The β-hydroxyarylethylimidazoles, enantiomorphs, acid addition salts and metal salt complexes of the present invention are useful as agricultural fungicides and as such can be applied to various loci such as the seed, the soil or the foliage. For such purposes these compounds can be used in the technical or pure form as prepared, as solutions or as formulations. The compounds are usually taken up in a carrier or are formulated so as to render them suitable for subsequent dissemination as fungicides. For example, these chemical agents can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in the case of foliar spray formulations, to include adjuvants, such as wetting agents, spreading agents, dispersing agents, stickers, adhesive and the like in accordance with agricultural practices. Such adjuvants commonly used in the art can be found in the John W. McCutcheon, Inc. publication "Detergents and Emulsifiers, Annual."

In general, the compounds of this invention can be dissolved in certain solvents such as acetone, methanol, ethanol, dimethylformamide, pyridine or dimethyl sulfoxide and such solutions can be extended with water. The concentrations of the solution can vary from about 1% to about 90% with a preferred range being from about 5% to about 50%.

For the preparation of emulsifiable concentrates, the compound can be dissolved in suitable organic solvents, or a mixture of solvents, together with an emulsifying agent which permits dispersion of the fungicide in water. The concentration of the active ingredient in emulsifiable concentrates is usually from about 10% to about 90% and in flowable emulsion concentrates, this can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of from about 20% to about 98%, preferably from about 40% to about 75%. A typical wettable powder is made by blending 50 parts of 1-[2-hydroxy-2-(2,4-dichlorophenyl)hexyl]imidazole, 45 parts of a synthetic precipitated hydrated silicon dioxide sold under the trademark Hi-Sil ®, and 5 parts of sodium lignosulfonate. In another preparation a kaolin type (Barden) clay is used in place of the Hi-Sil in the above wettable powder, and in another such preparation 25% of the Hi-Sil is replaced with a synthetic sodium silico aluminate sold under the trademark Zeolex ®7.

Dusts are prepared by mixing the β-hydroxyarylethylimidazoles, enantiomorphs, salts and complexes thereof with finely divided inert solids which can be organic or inorganic in nature. Materials useful for this purpose include botanical flours, silicas, silicates, carbonates and clays. One convenient method of preparing a dust is to dilute a wettable powder with a finely divided carrier. Dust concentrates containing from about 20% to about 80% of the active ingredient are commonly made and are subsequently diluted to from about 1% to about 10% use concentration.

The agronomically acceptable β-hydroxyarylethylimidazoles, enantiomorphs, salts and complexes thereof can be applied as fungicidal sprays by methods commonly employed, such as conventional high-gallonage hydraulic sprays, low-gallonage sprays, airblast spray, aerial sprays and dusts. The dilution and rate of application will depend upon the type of equipment employed, the method of application and diseases to be controlled, but the preferred fungicidally effective amount is usually from about 0.1 lb. to about 50 lbs. per acre of the active ingredient.

As a seed protectant, the amount of toxicant coated on the seed is usually at a dosage rate of from about 0.1 to about 20 ounces per hundred pounds of seed. As a soil fungicide the chemical can be incorporated in the soil or applied to the surface usually at a rate of from about 0.1 to about 50 lbs. per acre. As a foliar fungicide, the toxicant is usually applied to growing plants at a rate of from about 0.25 to about 10 lbs. per acre.

Fungicides which can be combined with the fungicides of this invention includes:

(a) dithiocarbamate and derivatives such as: ferric dimethyldithiocarbamate (ferbam), zinc dimethyldithiocarbamate (ziram), manganese ethylenebisdithiocarbamate (maneb) and its coordination product with zinc ion (mancozeb), zinc ethylenebisdithiocarbamate (zineb), zinc propylenebisdithiocarbamate (propineb), sodium methyldithiocarbamate (metham), tetramethylthiuram disulfide (thiram), the complex of zineb and polyethylene thiuram disulfide, 3,5-dimethyl-1,3,5-2H-tetrahydrothiadiazine-2-thione (dazomet); and mixtures of these and mixtures with copper salts;

(b) nitrophenol derivatives such as: dinitro-(1-methylheptyl) phenyl crotonate (dinocap), 2-sec-butyl-4,6-dinitrophenyl 3,3-dimethylacrylate (binapacryl), and 2-sec-butyl-4,6-dinitrophenyl isopropyl carbonate;

(c) heterocyclic structures such as: N-trichloromethylthiotetrahydrophthalimide (captan), N-trichloromethylthiophthalimide (folpet), 2-heptadecyl-2-imidazole acetate (glyodine), 2-octylisothiazol-3-one, 2,4-dichloro-6-(o-chloroanilino)-s-triazine, diethyl phthalimidophosphorothioate, 4-butyl-1,2,4-triazole, 5-amino-1-[bis(dimethylamino)phosphinyl]-3-phenyl-1,2,4-triazole, 5-ethoxy-3-trichloromethyl-1,2,4-thiadiazole, 2,3-dicyano-1,4-dithiaanthraquinone (dithianon), 2-thio-1,3-dithio-[4,5-b]quinoxaline (thioquinox), methyl 1-(butylcarbamoyl)-2-benzimidazole carbamate (benomyl), 2-(4′-thiazolyl) benzimidazole (thiabendazole), 4-(2-chlorophenylhydrazono)-3-methyl-5-isoxazolone, pyridine-2-thiol-1-oxide, 8-hydroxyquinoline sulfate and metal salts thereof; 2,3-dihydro-5-carboxanilido-6-methyl-1,4-oxathiin-4,4-dioxide, 2,3-dihydro-5-carboxanilido-6-methyl-1,4-oxathiin, α-(phenyl)-α-(2,4-dichlorophenyl)-5-pyrimidinyl-methanol (triarimol), cis-N-[(1,1,2,2-tetrachloroethyl)thio]-4-cyclohexene-1,2-dicarboxyimide, 3-[2-(3,5-dimethyl-2-oxycyclohexyl-2-hydroxy], -glutarimide (cycloheximide), dehydroacetic acid, N-(1,1,2,2-tetrachloroethylthio)-3a,4,7,7a-tetrahydrophthalimide (captafol), 5-butyl-2-ethylamino-4-hydroxy-6-methylpyrimidine (ethirimol), acetate of 4-cyclododecyl-2,6-dimethylmorpholine (dodemorph), and 6-methyl-2-oxo-1,3-dithiolo[4,5-b]quinoxaline (quinomethionate).

(d) miscellaneous halogenated fungicides such as: tetrachloro-p-benzoquinone (chloranil), 2,3-dichloro-1,4-naphthoquinone (dichlone), 1,4-dichloro-2,5-dimethoxybenzene (chloroneb), 3,5,6-trichloro-o-anisic acid (tricamba), 2,4,5,6-tetrachloroisophthalonitrile (TCPN), 2,6-dichloro-4-nitroaniline (dichloran), 2-chloro-1-nitropropane, polychloronitrobenzenes such as: pentachloronitrobenzene (PCNB) and tetrafluorodichloroacetone;

(e) fungicidal antibiotics such as: griseofulvin, kasugamycin and streptomycin;

(f) copper-based fungicides such as: cuprous oxide, basic cupric chloride, basic copper carbonate, copper naphthenate, and Bordeaux mixture; and (g) miscellaneous fungicides such as: diphenyl, dodecylguanidine acetate (dodine), phenylmercuric acetate, N-ethylmercuri-1,2,3,6-tetrahydro-3,6-endomethano-3,4,5,6,7,7,-hexachlorophthalimide, phenylmercuric monoethanol ammonium lactate, p-dimethylaminobenzenediazo sodium sulfonate, methyl isothiocyanate, 1-thiocyano-2,4-dinitrobenzene, 1-phenylthiosemicarbazide, nickel-containing compounds, calcium cyanamide, lime sulfur, sulfur, and 1,2-bis(3-methoxycarbonyl-2-thioureido) benzene (thiophanatemethyl).

The β-hydroxyarylethylimidazoles, enantiomorphs, addition salts and metal salt complexes of this invention can be advantageously employed in various ways. Since these compounds possess broad spectrum fungicidal activity, they can be employed in the storage of cereal grain. These compounds can also be employed as fungicides in turf, fruit orchards, vegetables and golf course applications. Other applications of the β-hydroxyarylethylimidazoles of this invention will suggest themselves to those skilled in the art of agriculture and horticulture.

We claim:

1. A compound of the formula

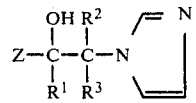

wherein Z is an unsubstituted phenyl or naphthyl group or a phenyl or naphthyl group substituted with up to three substituents selected from the group consisting of halogen, nitro, trihalomethyl, cyano, $(C_1-C_4)$alkyl, $(C_1-C_4)$alkoxy, $(C_1-C_4)$alkylthio, $(C_1-C_4)$alkylsulfinyl, $(C_1-C_4)$alkylsulfonyl, phenoxy, phenylthio, phenylsulfinyl, phenylsulfonyl and phenoxy, phenylthio, phenylsulfinyl or phenylsulfonyl substituted with up to two substituents selected from the group consisting of halogen, nitro, trifluoromethyl, cyano, methyl, methoxy, methylthio, methylsulfinyl and methylsulfonyl; $R^1$ is an unsubstituted phenyl or benzyl group or a phenyl or benzyl group substituted with up to two substituents selected from the group consisting of halogen, nitro, trihalomethyl, cyano, methyl, methoxy, methylsulfinyl and methylsulfonyl; and $R^2$ and $R^3$ are independently cyano, $(C_2-C_8)$alkenyl, $(C_5-C_8)$cycloalkenyl, $(C_2-C_8)$alkynyl, an unsubstituted phenyl or benzyl group or a phenyl or benzyl group substituted with up to two substituents selected from the group consisting of halogen, nitro, trihalomethyl, cyano, methyl, methoxy, methylsulfinyl and methylsulfonyl; and its agronomically acceptable enantiomorphs, acid addition salts and metal salt complexes thereof.

2. A compound of the formula

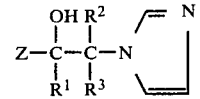

wherein Z is an unsubstituted phenyl group or a phenyl group substituted with up to two substitutents selected from the group consisting of halogen, nitro, trihalomethyl, cyano, $(C_1-C_4)$alkyl, $(C_1-C_4)$alkoxy, $(C_1-C_4)$alkylthio, $(C_1-C_4)$alkylsulfinyl, $(C_1-C_4)$alkylsulfonyl, phenoxy, phenylthio, phenylsulfinyl, phenylsulfonyl and phenoxy, phenylthio, phenylsulfinyl or phenylsulfonyl substituted with up to two substituents selected from the group consisting of halogen, nitro, trifluoromethyl, cyano, methyl, methoxy, methylthio, methylsulfinyl and methylsulfonyl; $R^1$ is cyano, $(C_2-C_8)$alkenyl, $(C_5-C_8)$cycloalkenyl or $(C_2-C_8)$alkynyl; and $R^2$ and $R^3$ are independently cyano, $(C_3-C_8)$cycloalkyl, $(C_2-C_8)$alkenyl, $(C_5-C_8)$cycloalkenyl, $(C_2-C_8)$alkynyl, an unsubstituted phenyl or benzyl group or a phenyl or benzyl group substituted with up to two substituents selected from the group consisting of halogen, nitro, trihalomethyl, cyano, methyl, methoxy, methylsulfinyl and methylsulfonyl.

3. A fungicidal composition which comprises, an agriculturally acceptable carrier and, as the active ingredient, a fungicidally effective amount of a compound according to claim 1.

4. A method for controlling phytopathogenic fungi comprising applying to a plant, a plant seed or a plant habitat a fungicidally effective amount of a compound having the structure

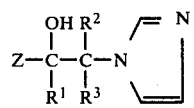

wherein Z is an unsubstituted phenyl or a phenyl substituted with up to three substituents selected from the group consisting of halogen, nitro, trihalomethyl, cyano, $(C_1-C_4)$alkyl, $(C_1-C_4)$alkoxy, $(C_1-C_4)$alkylthio, $(C_1-C_4)$alkylsulfinyl, $(C_1-C_4)$alkylsulfonyl, phenoxy, phenylthio, phenylsulfinyl or phenylsulfonyl substituted with up to two substituents selected from the group consisting of halogen, nitro, trifluoromethyl, cyano, methyl, methoxy, methylthio, methylsulfinyl and methylsulfonyl; $R^1$ is a cyano, $(C_2-C_{12})$alkyl, $(C_3-C_8)$cycloalkyl, $(C_2-C_8)$alkenyl, $(C_5-C_8)$cycloalkenyl or $(C_2-C_8)$alkynyl group; $R^2$ and $R^3$ are independently a hydrogen, cyano, $(C_3-C_8)$cycloalkyl, $(C_2-C_8)$alkenyl, $(C_5-C_8)$cycloalkenyl or $(C_2-C_8)$alkynyl, phenyl, benzyl, a substituted phenyl or a substituted benzyl group having up to three substituents selected from the group consisting of halogen, $(C_1-C_4)$alkyl and $(C_1-C_4)$alkoxy; or Z and $R^1$ when taken together form the group

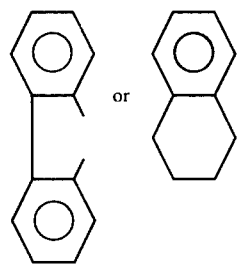

and the agronomically acceptable enantiomorphs, acid addition salts and metal salt complexes.

5. The method of claim 4 wherein Z is a phenyl group or a phenyl group substituted with up to three substituents selected from the group consisting of halogen, $(C_1-C_4)$alkyl and $(C_1-C_4)$alkoxy; $R^1$ is $(C_4-C_{12})$alkyl; and $R^2$ and $R^3$ are hydrogen.

6. The method of claim 5 wherein Z is a phenyl group or a phenyl group substituted with up to three substituents selected from the group consisting of chlorine, methyl and methoxy group; and $R^1$ is $(C_4-C_8)$alkyl.

7. The method of claim 6 wherein the compound has the structure

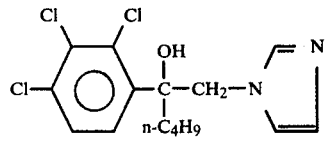

and agronomically acceptable salts thereof.

8. The method of claim 6 wherein Z is unsubstituted phenyl or phenyl substituted with up to three substituents selected from the group consisting of chlorine and methoxy; $R^1$ is butyl or octyl; and $R^2$ and $R^3$ are hydrogen.

9. The method of claim 8 wherein Z is phenyl, 2-chlorophenyl, 2,4-dichlorophenyl or 2,3,4-trichlorophenyl; $R^1$ is n-butyl or n-octyl; and $R^2$ and $R^3$ are hydrogen.

10. The method of claim 6 wherein the compound has the structure

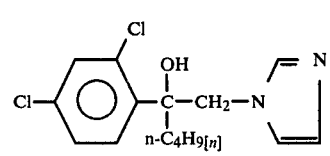

and agronomically acceptable salts thereof.

11. A method for controlling phytopathogenic fungi which comprises, applying to the plant, the plant seed or the plant habitat a fungicidally affective amount of a compound having the structure

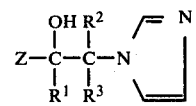

wherein Z is an unsubstituted phenyl or naphthyl group or a phenyl or naphthyl group substituted with up to three substituents selected from the group consisting of halogen, nitro, trihalomethyl, cyano, $(C_1-C_4)$alkyl, $(C_1-C_4)$alkoxy, $(C_1-C_4)$alkylthio, $(C_1-C_4)$alkylsulfinyl, $(C_1-C_4)$alkylsulfonyl, phenoxy, phenylthio, phenylsulfinyl, phenylsulfonyl and phenoxy, phenylthio, phenylsulfinyl or phenylsulfonyl substituted with up to two substituents selected from the group consisting of halogen, nitro, trifluoromethyl, cyano, methyl, methoxy, methylthio, methylsulfinyl and methylsulfonyl; $R^1$, $R^2$ and $R^3$ are independently hydrogen, cyano, $(C_2-C_{12})$alkyl, $(C_3-C_8)$cycloalkyl, $(C_2-C_8)$alkenyl, $(C_5-C_8)$cycloalkenyl, $(C_2-C_8)$alkynyl, an unsubstituted phenyl group or benzyl group or a phenyl or benzyl group substituted with up to two substituents selected from the group consisting of halogen, nitro, trihalomethyl, cyano, methyl, methoxy, methylsulfinyl and methylsulfonyl; or $R^1$ and Z when taken together form the group

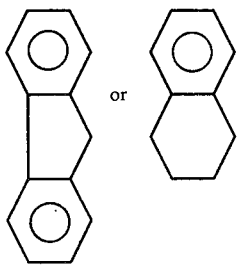

provided that when $R^2$ and $R^3$ are hydrogen, then $R^1$ is not hydrogen; and the agronomically acceptable salts thereof.

12. The method of claim 11 wherein Z is an unsubstituted phenyl group or a phenyl group substituted with up to three substituents selected from the group consisting of chlorine, methyl or methoxy; and $R^1$, $R^2$ and $R^3$ are independently hydrogen, $(C_4$–$C_8)$alkyl, an unsubstituted phenyl or benzyl group or a phenyl or benzyl group substituted with up to two chlorine substituents, provided that when $R^2$ and $R^3$ are hydrogen, then $R^1$ is not hydrogen.

13. A process for combating fungi in crops which comprises: applying to the crops to be protected against fungus attack a fungicidal formulation containing as the active ingredient a fungicidally effective amount of an imidazole derivative of the formula

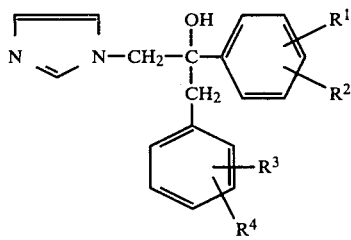

wherein $R^1$ is halogen or methoxy and $R^2$, $R^3$ and $R^4$ are hydrogen or halogen, or an agriculturally acceptably salt thereof.

* * * * *

UNITED STATES PATENT AND TRADEMARK OFFICE
CERTIFICATE OF CORRECTION

PATENT NO. : 4,413,003
DATED : November 1, 1983
INVENTOR(S) : George A. Miller et al.

It is certified that error appears in the above—identified patent and that said Letters Patent is hereby corrected as shown below:

Column 18, claim 10, structure

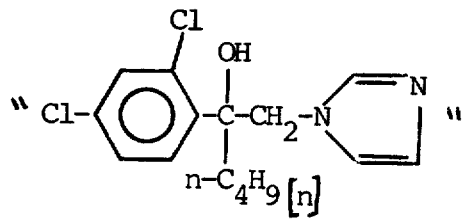 should read 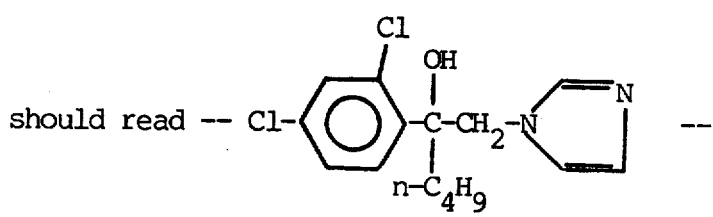

Signed and Sealed this

Fifteenth Day of May 1984

[SEAL]

Attest:

Attesting Officer

GERALD J. MOSSINGHOFF
Commissioner of Patents and Trademarks